(12) United States Patent
Levantino et al.

(10) Patent No.: US 9,615,977 B2
(45) Date of Patent: Apr. 11, 2017

(54) SANITARY DEVICE

(71) Applicant: PNP LLC, Montgomery, TX (US)

(72) Inventors: Patrick M. Levantino, Montgomery, TX (US); Nickolas J. Levantino, Montgomery, TX (US)

(73) Assignee: Triple L Holdings, Inc., Conroe, TX (US)

( * ) Notice: Subject to any disclaimer, the term of this patent is extended or adjusted under 35 U.S.C. 154(b) by 329 days.

(21) Appl. No.: 14/298,142

(22) Filed: Jun. 6, 2014

(65) Prior Publication Data

US 2015/0351974 A1 Dec. 10, 2015

(51) Int. Cl.
*A61F 13/20* (2006.01)
*A61F 13/26* (2006.01)

(52) U.S. Cl.
CPC ........ *A61F 13/2074* (2013.01); *A61F 13/202* (2013.01); *A61F 13/2011* (2013.01); *A61F 13/266* (2013.01); *A61F 13/2071* (2013.01)

(58) Field of Classification Search
CPC .. A61F 13/2011; A61F 13/202; A61F 13/266; A61F 13/2071; A61F 13/2074
USPC ...................... 604/1–11, 385.17, 385.18, 904
See application file for complete search history.

(56) References Cited

U.S. PATENT DOCUMENTS

| 1,561,020 | A | | 11/1925 | Pond | |
| 4,209,009 | A | | 6/1980 | Hennig | |
| 4,286,596 | A | | 9/1981 | Rubinstein | |
| 4,445,899 | A | | 5/1984 | Bond | |
| 5,016,651 | A | * | 5/1991 | Stalcup | ............... A61M 35/006 128/898 |
| 2003/0045829 | A1 | * | 3/2003 | Gehling | .............. A61F 13/2051 604/11 |

OTHER PUBLICATIONS

Article on www.ehow.com; "What Is Telfa?" pp. 1-2.

* cited by examiner

*Primary Examiner* — Jacqueline Stephens
(74) *Attorney, Agent, or Firm* — Tumey L.L.P.

(57) ABSTRACT

A sanitary device for insertion into a body cavity having a perforated casing in which a medicant is located within a distal portion of the casing and a semi-rigid absorbent material is located within a proximal portion of the casing. A plunger extends into the casing from the proximal portion and is movable to force the semi-rigid absorbent material into contact with the medicant which forces the medicant out of the distal portion of the casing. Unwanted body fluids can drain into the proximal portion and are absorbed by the semi-rigid absorbent material.

A second embodiment of the invention includes an applicator for inserting a body insert into the body cavity. The body insert includes a semi-rigid absorbent material surrounded by a thin sheet of a lubricating material such as Telfa. The body insert may also include a medicant.

14 Claims, 2 Drawing Sheets

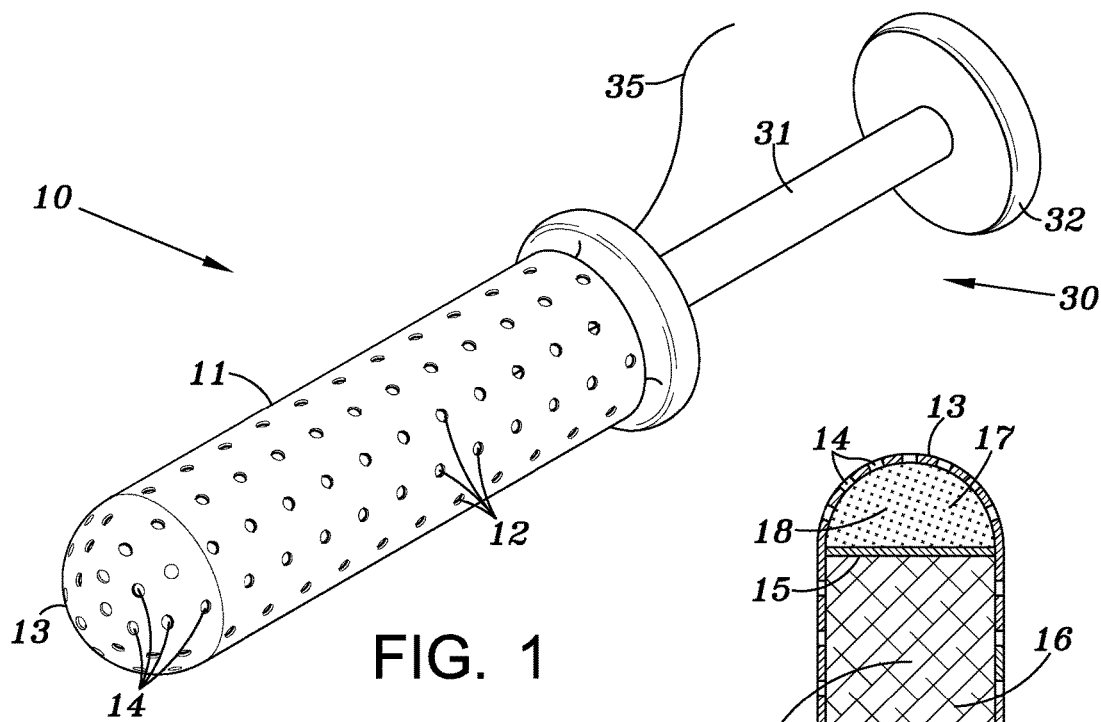
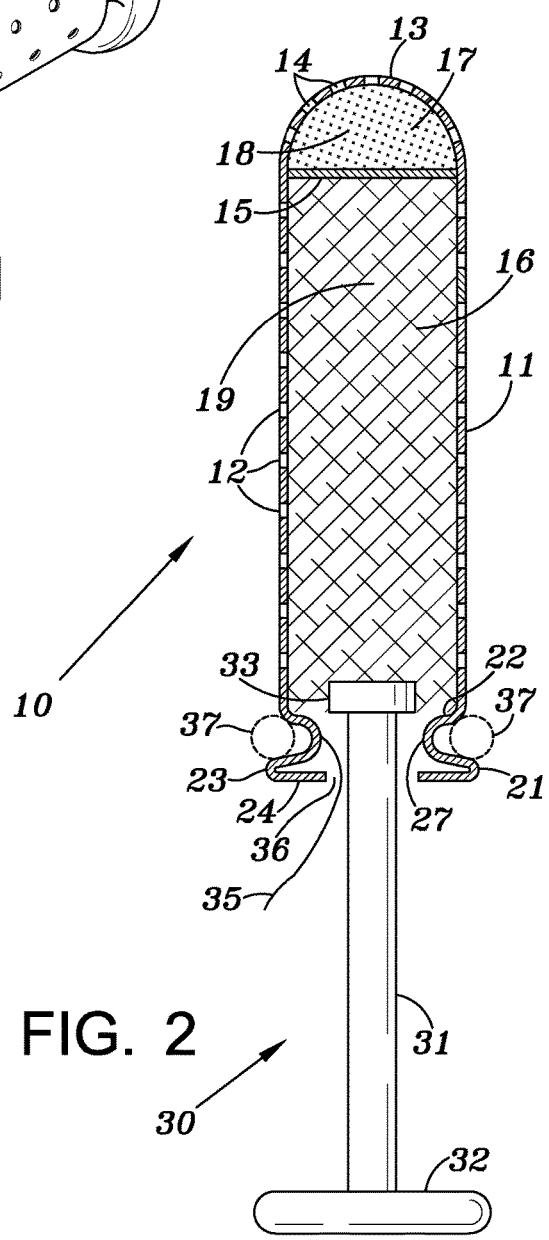
FIG. 1
FIG. 2

SANITARY DEVICE

BACKGROUND OF INVENTION

1. Field of the Invention

This invention relates to a vaginal or rectal tampon that serves the dual purpose of delivering a dose of a medicant or other material into a respective body cavity and also serves to accumulate body fluid that exits the cavity through human biological processes.

2. Description of Related Art

U.S. Pat. No. 4,286,596 discloses a tampon for entry into a body cavity that includes a frangible reservoir containing medicant. In use the reservoir is ruptured by the user prior to or during insertion. The medicant is absorbed by the tampon body which when inserted into the body cavity contacts, for example, hemorrhoidal veins. The medicant which is absorbed by the tampon body is thus brought into contact with the area of the body to be treated.

U.S. Pat. No. 1,561,020 to Pond discloses a rectal tampon which includes a shell of gelatin or soluble material, a body of cotton or wool material and a body of medicated material. The outer shell of the tampon is designed to be dissolved.

BRIEF SUMMARY OF THE INVENTION

The invention disclosed and claimed herein is directed to a dual purpose tampon that includes a first distal portion adapted to deliver a medicant or other material into a body cavity and also includes a second proximal portion which is adapted to absorb any unwanted fluid discharge from the cavity due to biological or natural processes.

The device includes an outer perforated casing which may be formed of a rigid, semi-rigid or flexible material. The casing provides support for a gel material which includes the medicant or other liquid and the casing also supports a semi-rigid body of absorbent material for absorbing any unwanted bodily fluid discharge.

The device further includes a plunger having a piston head located within the casing. The plunger is adapted to be moved by the user to force the gel material through openings provided in the distal portion of the casing. The proximal portion of the casing is also provided with a plurality of openings which allow for passage of bodily fluids into the lower portion of the casing. These fluids are absorbed by the absorbent material positioned or located within the proximal portion of the casing.

BRIEF DESCRIPTION OF THE SEVERAL VIEWS OF THE DRAWING(S)

FIG. 1 is a perspective view of an embodiment of the invention.

FIG. 2 is a cross-sectional view of the embodiment of FIG. 1.

DETAILED DESCRIPTION OF THE INVENTION

Figure 3:
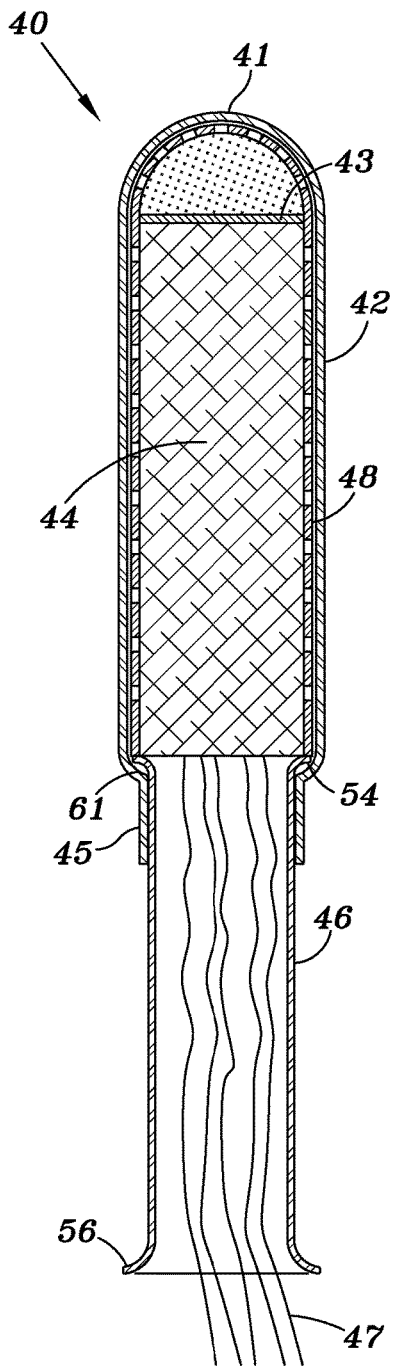
FIG. 3 is a cross-sectional view of a second embodiment of the invention.

Referring to FIGS. 1 and 2, the sanitary device 10 according to an embodiment of the invention includes a casing 11, which includes a plurality of openings 12 in a proximal portion of the casing and a plurality of openings 14 located at a distal portion 13 of the casing. Casing 11 may be rigid, semi-rigid or flexible and may be consist of a plastic material.

A thin membrane 15 may be positioned within casing 11 to form a distal chamber 17 and a proximal chamber 16. Material such as a gel 18 containing a medicant or other liquid is located within chamber 17 and an absorbent material 19 such as cotton or wool is located within chamber 16.

Absorbent material 19 is formed as a semi-rigid mass so as to be capable of rupturing membrane 15.

The lower portion of casing 11 as shown in FIG. 2 has a inwardly curved portion 22 followed by an outwardly curved portion 21 which curves inwardly again at 24. This forms a groove at 27 which is an adapted to receive the sphincter muscle 37 shown in phantom of the anus.

The sanitary device also includes a plunger member 30 having a stem portion 31 which extends outwardly from an opening 36 in the lower or proximal portion of casing 11. Plunger 31 also includes a piston head 33 which is positioned within chamber 16 and engages the absorbent member 19. A finger engaging portion 32 is located at an end of the plunger.

Piston member 33 may be releasably secured to the absorbent material by a weak adhesive bond. The diameter of piston 33 is slightly less than that of opening 36 so that it may be withdrawn from chamber 16 in a manner to be described below. A string 35 is secured to the device as is known in the art for easy removal of the device from the body cavity.

The distal portion 13 may be covered with a suitable seal to prevent contamination and the entire tampon can be packaged in a sterilized sealed wrapper.

In use, the tampon 10 is removed from its package and inserted into a body cavity. The user will depress plunger 30 which will cause absorbent member 19 to rupture membrane 15 and force gel material outwardly through apertures 14. Thus the gel material with a medicant or other liquid will be positioned in close proximity to the walls of the cavity. Plunger 30 can then be within entirely from the device and discarded. Any unwanted discharge of bodily fluids from the cavity will be directed inwardly through opening 12 into the interior of chamber 19. The fluids will be absorbed by absorbent member 19.

After use, the user may remove the tampon from the body cavity by grasping string 35.

A second embodiment of the invention will now be described with respect to FIGS. 3-5.

Figure 4:
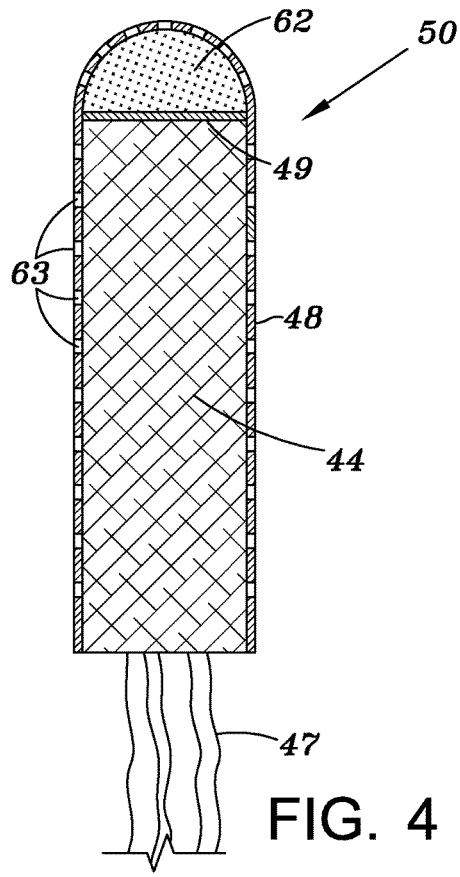
FIG. 4 is a cross-sectional view of the portion of the sanitary device that remains in the body cavity.
Figure 5:
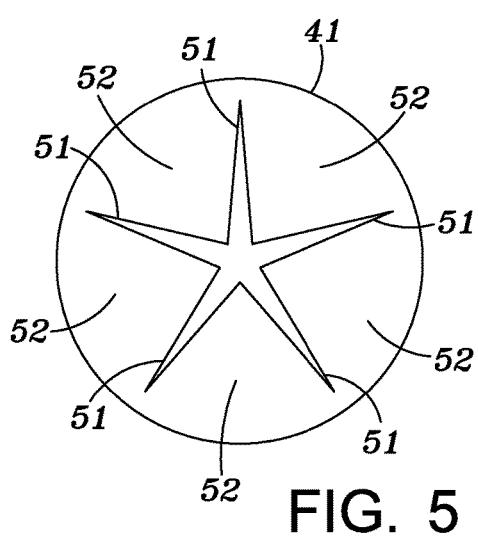
FIG. 5 is a top view of the sanitary device shown in FIG. 3.

The embodiment of FIGS. 3-5 includes an application device including an outer, generally cylindrical casing having a first distal portion 42 and a second proximal portion 45 of a reduced diameter with respect to the diameter of portion 42. The outer casing is formed of a relatively thin plastic material.

A plunger 46 having flared ends at 54 and 56 is positioned within the outer casing and is adapted to be slidably movable within the outer casing. The flared ends of plunger 46 prohibit the plunger from being withdrawn from the casing or pushed through the resilient flaps 52 at the top of the outer casing as discussed below. Flared end 54 of plunger 46 also engages semi-rigid absorbent mass 44 and pushes it out the top of distal portion 42 when plunger 46 is depressed.

The upper tip portion 41 of the outer casing is generally semi-spherical and includes a plurality of slits 51 as seen in FIG. 5. These slits form a plurality of flaps which will flex outwardly as a force is applied from within the casing. The general structure of the outer casing and plunger is commonly in use as an applicator for feminine hygiene products such as tampons.

FIG. 4 illustrates the portion of the sanitary device that remains in the body cavity. It includes a semi-solid mass of an absorbent material such as cotton and may be formed of compressed cellulose material commonly used for tampons.

Absorbent body 44 is sufficiently rigid to maintain its shape during insertion. A thin plastic material 48 surrounds the absorbent body. Plastic material 48 includes a plurality of tiny perforations 63 which allows fluid to pass from the body cavity into the absorbent material 44. Layer 48 is made from a thin plastic film that has lubricating characteristics so as to facilitate insertion and removal of the sanitary device into and out of the body cavity. An example of such a material is Telfa® which is made by the Kendall Company Ltd. It consists of polyethylene terephthalate.

The upper portion 62 of the body insert 50 may contain a suitable medicant for example Zylocaine gel 2% or Lidocaine 2% gel. A membrane 49 separates the medicant 62 from body 44. A string 47 is securely attached to the absorbent mass 44 for removal of the body insert 50 after a given time period of use.

MODE OF OPERATION

The user may hold reduced diameter portion 45 of the outer casing with their forefingers and insert the outer housing into the body cavity a distance of about ¼". Using a thumb of the user, plunger 46 is slowly depressed such that it engages the lower end of body insert 50 which in turn will exert a force on flaps 52 at the distal end of the outer casing.

This force will cause the flaps to expand outwardly thereby permitting the body insert 50 to exit the outer casing into the body cavity. Outer housing 42 and plunger 46 can now be removed from the body cavity leaving behind the body insert. The insert can be removed by grasping string 47 which remains outside the body cavity.

As stated above, the upper and lower ends of plunger 46 are flared. The flaring at 54 prevents removal of the plunger from the outer casing since it engages an internal shoulder 61 at the juncture of the outer casing sections. In like manner, flaring 56 will prevent plunger 46 from passing through lower casing portion 45.

Although the present invention has been described with respect to specific details, it is not intended that such details should be regarded as limitations on the scope of the invention, except to the extent that they are included in the accompanying claims.

We claim:

1. A sanitary device for insertion into and retention within a body cavity comprising:
    a casing that remains in the body cavity during use having a distal portion and
    a proximal portion having a bottom open end;
    the distal portion including a plurality of openings;
    the proximal portion having a plurality of openings;
    an absorbent, relatively rigid mass of material located within the distal portion of the casing; and
    a plunger extending through the open bottom end of the casing whereby when said plunger is pushed by a user, it contacts the absorbent relatively rigid mass which is axially moved to displace the medicant through the openings located in the distal portion of the casing.

2. The sanitary device of claim 1 wherein a lower portion of the proximal casing includes a first inwardly projecting portion and a second outwardly projecting portion that form a groove, the groove being adapted to be positioned within the sphincter muscle of the anus.

3. A sanitary device as claimed in claim 1 wherein the distal portion of the casing has a semi-spherical shaped tip.

4. A sanitary device as claimed in claim 1 wherein the proximal portion of the casing has a generally cylindrical shape.

5. A sanitary device as claimed in claim 1 further including a medicant positioned within the distal portion of the casing.

6. A sanitary device as claimed in claim 5 further including a frangible membrane separating the medicant from the absorbent relatively rigid mass of material.

7. The sanitary device as claimed in claim 1 wherein the casing is formed as a cylindrical tube and the openings in the distal and proximal portions are formed through a surface of the tube.

8. A sanitary device comprising:
    an outer applicator housing having a distal portion and a proximal portion, the distal portion having an opening for dispensing a body insert and the proximal portion having an opening for a plunger,
    the plunger recipically positioned within the outer applicator housing;
    the body insert located within the outer applicator casing and including a semi-rigid absorbent material;
    a thin sheet of lubricating material having a plurality of small apertures surrounding the absorbent material; and
    a string secured to the body insert.

9. A sanitary device according to claim 8 wherein the thin sheet of plastic material comprises polyethylene terephthalate.

10. A sanitary device according to claim 8 further including a medicant located within the body insert.

11. A sanitary device according to claim 10 wherein the medicant is a 2% Zylocaine gel.

12. A sanitary device according to claim 10 wherein the medicant is 2% Lidocaine gel.

13. The sanitary device as claimed in claim 10, wherein the body insert include a proximal portion and a distal portion separated by a frangible membrane positioned within the body insert; and extending across a chamber located within the body insert and the medicant is located within the distal portion of the body insert.

14. The sanitary device as claimed in claim 13 wherein the semi-rigid absorbent material is located within the proximal portion of the body insert.

* * * * *